United States Patent [19]

Hargis

[11] Patent Number: 4,562,296
[45] Date of Patent: Dec. 31, 1985

[54] PRODUCTION OF ALDEHYDES AND KETONES

[75] Inventor: Duane C. Hargis, Baton Rouge, La.
[73] Assignee: Ethyl Corporation, Richmond, Va.
[21] Appl. No.: 671,172
[22] Filed: Nov. 13, 1984
[51] Int. Cl.$^4$ .............................................. C07C 45/45
[52] U.S. Cl. .................................. 568/388; 568/391; 568/458; 568/465; 568/403
[58] Field of Search ............... 568/465, 403, 458, 391, 568/388

[56] References Cited

U.S. PATENT DOCUMENTS

| | | | |
|---|---|---|---|
| 1,944,109 | 1/1934 | Roka | 568/388 |
| 1,961,912 | 6/1934 | Querfurth | 568/403 |
| 1,970,782 | 8/1934 | Swallen | 568/388 |
| 1,978,404 | 10/1934 | Bloomfield et al. | 568/403 |
| 1,978,619 | 10/1934 | Bloomfield et al. | 568/403 |
| 2,002,794 | 5/1935 | Querfurth | 568/388 |
| 2,064,254 | 12/1936 | Fuchs et al. | 568/391 |
| 2,587,576 | 3/1952 | Field | 568/458 |
| 2,697,730 | 12/1954 | Mecorney et al. | 568/391 |
| 2,725,400 | 11/1955 | Mecorney et al. | 568/391 |
| 3,875,239 | 4/1975 | Stouthamer et al. | 568/391 |
| 4,351,958 | 7/1982 | Takahota et al. | 564/409 |

FOREIGN PATENT DOCUMENTS 56-110634 9/1981 Japan .
57-11933 1/1982 Japan .

Primary Examiner—James H. Reamer
Attorney, Agent, or Firm—Donald L. Johnson; John F. Sieberth

[57] ABSTRACT

One or more aldehydes or ketones, or both, are produced by pyrolyzing an alcohol having at least two carbon atoms or an aldehyde having at least two carbon atoms, or both, over a Group VIII metal oxide catalyst, preferably a catalyst composed predominantly of iron oxide, notably ferric oxide. Preferably, the catalyst additionally contains a minor proportion of a Group IV-A metal oxide, most preferably germanium dioxide. The process provides a good yield of lower molecular weight aldehydes, such as formaldehyde, or higher molecular weight ketones, such as acetone, 2-pentanone and the like. Selective manufacture of products enriched either in aldehyde or in ketone can be achieved by a simple adjustment in the reaction conditions employed.

16 Claims, No Drawings

PRODUCTION OF ALDEHYDES AND KETONES

FIELD OF THE INVENTION

This invention relates to a novel catalytic process for the production of aldehydes and ketones.

BACKGROUND

Various industrial processes exist for the manufacture of formaldehyde and methyl ketones, notably acetone, methyl ethyl ketone and methyl isobutyl ketone.

The most common method for manufacturing formaldehyde involves the oxidation of methanol with air over a suitable catalyst. In one such method a rich methanol-air mixture is passed over a platinum catalyst at 635° C. A newer method of this type involves use of a lean methanol-air mixture and a ferric oxide-molybdenum oxide catalyst. Controlled air-oxidation of methane is another satisfactory method for producing formaldehyde.

To synthesize acetone, dehydrogenation of isopropanol is a commonly used procedure. Dehydrogenation of sec-butanol or the oxidation of butane are commercially feasible methods for producing methyl ethyl ketone, whereas catalytic reduction of mesityl oxide is a common way of producing methyl isobutyl ketone.

THE INVENTION

This invention involves the discovery of a unique catalytic process by which alcohols or aldehydes, or mixtures of both, may be converted in good yield to lower molecular weight aldehydes, such as formaldehyde, or to higher molecular weight ketones, such as acetone, 2-pentanone and the like. A feature of this invention is that the process enables the selective manufacture of products enriched either in aldehyde or in ketone by a simple adjustment in the reaction conditions employed.

Unlike most prior processes, the process of this invention involves a catalytic pyrolysis operation wherein the alcohol/aldehyde feed can be passed over the catalyst in the substantial absence of air. However the introduction of air into the reaction system is not prejudicial.

In accordance with this invention one or more aldehydes or ketones, or both, are produced by pyrolyzing an alcohol having at least two carbon atoms or an aldehyde having at least two carbon atoms, or both, over a Group VIII metal oxide catalyst, preferably a catalyst composed predominantly of iron oxide, notably ferric oxide.

In a preferred embodiment, the catalyst additionally contains a minor proportion of a Group IV-A metal oxide, most preferably a germanium oxide. These and other preferred embodiments of my invention will become still further apparent from the ensuing description and appended claims.

The present invention is carried out at an elevated temperature suitable for catalytic pyrolysis processes. In general, the reaction temperature will usually be about 200° C. or higher, preferably 250° or higher. More preferably, the process is carried out at an elevated temperature in the range of about 300°–500° C. While higher temperatures may be used, the temperature used should take into consideration the thermal decomposition temperatures of the products as well as the effect of temperature on the activity of the particular heterogeneous catalyst system being employed.

The process of this invention is suitably carried out at atmospheric pressure but may be carried out at superatmospheric or subatmospheric pressures.

Various alcohols and mixtures of alcohols are usable according to the present invention. These include aliphatic alcohols and alicyclic alcohols. Useful aliphatic alcohols include alkanols, alkenols and alkynols, such as ethanol, propanol, isopropanol, butanol, pentanol, 3-methyl-1-butanol, hexanol, 3,3-dimethyl-1-butanol, heptanol, octanol, 2-ethoxyethanol, 2-butoxyethanol, 2-(2-ethoxyethoxy)ethanol, allyl alcohol, crotyl alcohol, 3-buten-1-ol, methallyl alcohol, 3-penten-1-ol, 4-penten-1-ol, 2-hexen-1-ol, 3-hexen-1-ol, propargyl alcohol, phenethyl alcohol, and the like. Primary and secondary alkanols having at least two carbon atoms and a boiling point (at atmospheric pressure) no higher than about 250° C. are preferred. Especially preferred are $C_2$–$C_{10}$ alkanols such as ethanol, propanol, isopropanol, butanol, sec-butanol, hexanol, octanol, 2-ethylhexanol, decanol, and the like.

Alicyclic alcohols usable according to the present invention include the cycloalkanols, cycloalkenols and cycloalkynols, and their ring-substituted congeners, such as cyclobutanol, cyclopentanol, cyclohexanol, cyclooctanol, 2-methylcyclobutanol, 3-methylcyclobutanol, cyclopentanol, 2-methylcyclopentanol, 3-methylcyclopentanol, cyclohexanol, cyclooctanol, cyclopentenol, cyclohexenol, cyclooctynol, and the like.

Aldehydes that may be employed in the process of this invention are exemplified by acetaldehyde, propionaldehyde, butyraldehyde, isobutyraldehyde, 2-methylbutanal, acrolein, citral, crotonaldehyde, glyoxal, methacrolein, octanal, pyruvic aldehyde, and other similar straight or branched chain aliphatic aldehydes having at least 2 carbon atoms and a boiling point (at atmospheric pressure) no higher than about 250° C. Mixtures of aldehydes may be used, if desired. Especially preferred are the $C_2$–$C_6$ alkanals.

In conducting the process of this invention, the inclusion of water in the feed to the catalyst constitutes a preferred embodiment, especially when the feedstock is acetaldehyde, as this tends to significantly increase the yield of formaldehyde or methyl ketones, whichever is desired. When water is employed, it will normally be used in amounts no higher than about 10 moles per mole of alcohol or aldehyde used, preferably in amounts falling in the range of about 0.1 to about 5 moles per mole of alcohol or aldehyde used.

The present invention is capable of being carried out in either a batch or continuous operation mode according to the available equipment and intentions of the operator.

According to the invention, various catalysts may be used so long as the catalyst, which consists essentially of a Group VIII metal oxide, preferably with a minor proportion of a Group IV-A metal oxide, has suitable activity for the pyrolysis.

As is well known, Group VIII is composed or iron, cobalt, nickel, ruthenium, rhodium, palladium, osmium, iridium and platinum. The Group IV-A metals are silicon, germanium, tin and lead.

Mixtures of various oxides of these respective groups of metals the form viable catalysts for the pyrolysis are within the ambit of this invention. Thus in the case of the Group VIII oxides, the catalysts may be composed of mixtures of different oxides of the same metal (e.g., $Fe_2O_3$ and $FeO$, $Ni_2O_3$ and $NiO$, etc.). Likewise, mixtures composed of oxides of different metals of Group VIII (e.g., $Fe_2O_3$ and $Ru_2O_3$, $Fe_2O_3$ and $Co_2O_3$, $Ru_2O_3$ and $Os_2O_3$, etc.) may be used. Similarly, in the case of the Group IV-A metal oxide portion of the Group VIII-/IV-A mixed oxide catalyst, different oxides of the same Group IV-A metal (e.g., $GeO_2$ and $GeO$, $SnO_2$ and $SnO$, etc.) and oxides of different Group IV-A metals (e.g., $GeO_2$ and $SnO_2$, $SiO_2$ and $GeO_2$, etc.) may be used. Catalysts in which a major portion of the active catalyst is one or more oxides of one or more Group VIII metals and a minor portion of the catalyst is one or more oxides of one or more B-subgroup metals plus one or more oxides of one or more Group IV-A metals are also deemed feasible.

Some examples of mixed oxide catalyst that may be used in the practice of this invention include:

| | |
|---|---|
| $Fe_2O_3$—$SiO_2$ | $Co_2O_3$—$TiO_2$—$SiO_2$ |
| $Co_2O_3$—$SiO_2$ | $Ni_2O_3$—$ZrO_2$—$SiO_2$ |
| $Ni_2O_3$—$SiO_2$ | $Ru_2O_3$—$V_2O_3$—$SiO_2$ |
| $Ru_2O_3$—$SiO_2$ | $Fe_2O_3$—$MnO_2$—$GeO_2$ |
| $Fe_2O_3$—$GeO_2$ | $Fe_2O_3$—$Cr_2O_3$—$GeO_2$ |
| $Co_2O_3$—$GeO_2$ | $Fe_2O_3$—$MoO_3$—$GeO_2$ |
| $Ni_2O_3$—$GeO_2$ | $Co_2O_3$—$TiO_2$—$GeO_2$ |
| $Ru_2O_3$—$GeO_2$ | $Ni_2O_3$—$ZrO_2$—$GeO_2$ |
| $Fe_2O_3$—$SnO_2$ | $Ru_2O_3$—$V_2O_3$—$GeO_2$ |
| $Co_2O_3$—$SnO_2$ | $Fe_2O_3$—$MnO_2$—$SnO_2$ |
| $Ni_2O_3$—$SnO_2$ | $Fe_2O_3$—$Cr_2O_3$—$SnO_2$ |
| $Ru_2O_3$—$SnO_2$ | $Fe_2O_3$—$MoO_3$—$SnO_2$ |
| $Fe_2O_3$—$PbO_2$ | $Co_2O_3$—$TiO_2$—$SnO_2$ |
| $Co_2O_3$—$PbO_2$ | $Ni_2O_3$—$ZrO_2$—$SnO_2$ |
| $Ni_2O_3$—$PbO_2$ | $Ru_2O_3$—$V_2O_3$—$SnO_2$ |
| $Ru_2O_3$—$PbO_2$ | $Fe_2O_3$—$MnO_2$—$PbO_2$ |
| $Rh_2O_3$—$GeO_2$ | $Fe_2O_3$—$In_2O_3$—$SnO_2$ |
| $PdO$—$GeO_2$ | $Co_2O_3$—$MoO_3$—$MnO_2$—$SiO_2$ |
| $OsO_2$—$GeO_2$ | $Ni_2O_3$—$WO_3$—$TiO_2$—$SiO_2$ |
| $OsO_2$—$SnO_2$ | $Ru_2O_3$—$MoO_3$—$ZrO_2$—$SiO_2$ |
| $IrO_2$—$GeO_2$ | $OsO_2$—$WO_3$—$V_2O_3$—$SiO_2$ |
| $PtO_2$—$GeO_2$ | $PtO_2$—$MoO_3$—$MnO_2$—$GeO_2$ |
| $PtO_2$—$SnO_2$ | $PtO_2$—$TiO_2$—$ZrO_2$—$GeO_2$ |
| $PtO_2$—$PbO$ | $Fe_2O_3$—$Cr_2O_3$—$ZrO_2$—$GeO_2$ |
| $Fe_2O_3$—$MnO_2$—$SiO_2$ | $Co_2O_3$—$MoO_3$—$V_2O_3$—$GeO_2$ |
| $Fe_2O_3$—$Cr_2O_3$—$SiO_2$ | $Ni_2O_3$—$Cr_2O_3$—$MnO_2$—$SnO_2$ |
| $Fe_2O_3$—$MoO_3$—$SiO_2$ | |

Various other oxides usable as additional components of the catalysts of the present invention such as one or more oxides of aluminum, antimony, arsenic, barium, beryllium, bismuth, calcium, copper, gallium, lithium, magnesium, potassium, sodium, thorium, zinc, and the like, may be prepared by any of the known means and combined with the Group VIII metal oxide catalysts according to the invention.

As noted above, a preferred group of catalysts are those composed of one or more Group VIII metal oxides in combination with one or more Group IV-A metal oxides (with or without additional B- and/or A-subgroup metal oxides). These should predominate (on a weight basis) in the VIII subgroup metal oxide(s) and should contain a minor proportion of Group IV-A metal oxide(s). Particularly preferred catalysts include those consisting essentially of at least about 60% by weight of Group VIII oxide(s), about 1 to about 40% by weight of Group IV-A metal oxide(s) and the balance, if any, being essentially one or more other metal oxides. The most preferred catalyst of this invention consist essentially of an oxide of iron, especially ferric oxide, particularly those in which the iron oxide is in combination with one or more oxides of silicon, germanium and tin, especially $GeO_2$. An example is a catalyst that contains at least about 90% by weight of ferric oxide and up to about 10% by weight of germanium dioxide.

Methods for the manufacture of metal oxides are known and reported in the literature. When utilizing such procedures care should be taken to avoid heating the oxide catalyst to a temperature which destroys or substantially diminishes its catalytic activity in my pyrolysis process. The catalyst may be supported on or impregnated onto a suitable inert carrier although this is ordinarily unnecessary.

Although the process can be carried out in the liquid phase, it is preferable to conduct the process in the vapor phase using a fixed bed or a moving or fluidized bed of the catalyst.

The present invention will be still further understood by a review of the following illustrative examples of the best mode of the invention of which I am now aware, in which all of the percentages are expressed on a weight basis.

In the runs referred to in the ensuing examples, use was made of a tubular reactor positioned within an Ohio Thermal wire wound tubular furnace, model T11C-0432. The muffle tube of the furnace was 1½ inches inside diameter and 12 inches long, constructed of fused alumina. A ¼ inch inside diameter thermocouple well was provided adjacent to the heating element. The thermocouple was used to control the series 4DA controller which has a range of 200°–1100° C. The reactor itself was a 19 inch long, 1 inch inside diameter stainless steel tube fitted with an internal thermocouple well. The reactor tube was fitted for supply of helium gas from one line and a second line connected to a Milton Roy pump. The second line fed reactants from a reservoir attached thereto. A water condenser below the reactor tube and an ice bath were used to collect liquid in glassware in the ice bath. The vapors transmitted from the glassware in the ice bath were directed to a dry ice bath and the outlet thereof was connected directly to a gas chromatography unit and then to a wet test meter.

The following procedure was used in the runs referred to hereinafter. The reactor tube was filled with 5 millimeter glass beads to define the catalyst bed location. A weighed amount of catalyst was then supplied to the catalyst bed area and additional 5 millimeter beads were used to fill the tube to the top of the furnace. All equipment was properly purged and flushed according to good standard laboratory practice. The desired feed for the run was added to the reservoir and the pump and inlet tube as necessary. The ice water bath and dry ice bath were attached, and the helium flush was started at the rate of 20–30 cc per minute during furnace warmup and stabilization. To start a run, the helium was turned off, and the feed pump was turned on at the desired feed rate. The thermocouple temperatures were recorded along with the feed level and the wet test meter readings. The sampling times were also noted. The product gases were directed to the sample loop of the GC sampling valve and injected onto a 10′×⅛″ Poropak ™ R column. The traps were removed and immediately replaced with a second set. The liquid samples were combined and weighed. To terminate the run, the feed pumps were turned off and drained for about five minutes before removing the residue therein. Thereafter, the helium flush was again turned on at about 20–30 cc per minute and the furnace was turned off. After cooling to room temperature, the reactor tube was removed for catalyst inspection, analysis, and/or replacement.

EXAMPLE I

Catalyst Preparation

A preferred catalyst of this invention was prepared in the following manner. One liter of a 0.5 molar aqueous solution of $FeNH_4(SO_4)_2$ was taken to a pH of 12.5 by dropwise addition of one liter of 4N NaOH solution. The treated solution was heated to 90°–93° C. for one hour, then allowed to stand overnight. The precipitate was filtered, washed, dried at 95° C., and ground to −100 mesh. The ground precipitate ws then added to 0.936 g of $GeO_2$ dissolved in 1155 mL of distilled water, and the water was removed by heating. The resultant catalyst was dried for two hours at 100° C., and then calcined overnight at 350° C. to give the finished catalyst. It contained 96.1 weight % $Fe_2O_3$ and 3.9 weight % $GeO_2$.

Pyrolysis Reactions

Using the apparatus and procedure described above, a series of four runs was made at 350° C. In each run the feed was passed in the vapor phase over the above $Fe_2O_3$-$GeO_2$ catalyst at the rate of 4 mL/hr. The following feeds were used:

Run No. 1—Ethanol (EtOH)
Run No. 2—Acetaldehyde (AcH)
Run No. 3—Acetaldehyde & ethanol (equimolar mixture)
Run No. 4—Acetaldehyde & water (equimolar mixture)

The results for three runs are set forth in Table 1 in which MEK stands for methyl ethyl ketone and EtOAc stands for ethyl acetate. It will be noted from these data that at 350° C. the catalyst caused the formation of a substantial proportion of formaldehyde.

TABLE 1

Catalyzed Pyrolysis of Acetaldehyde & Ethanol
350° C.

| Run Number | 1 | 2 | 3 | 4 |
|---|---|---|---|---|
| Feed | EtOH | AcH | AcH & EtOH | AcH & H₂O |
| EtOH Conversion, % | 30.4 | — | 19.2 | — |
| AcH Conversion, % | — | 78.3 | 89.4 | 81.0 |
| Product Distribution, wt. percent | | | | |
| CO | 1.0 | 0.1 | 5.4 | 0.1 |
| CO₂ | 11.2 | 5.9 | 6.5 | 4.5 |
| CH₄ | 0.4 | 0.8 | 0.7 | 0.5 |
| C₂-C₄ HC | 5.8 | 0.3 | 1.1 | 0.2 |
| HCHO | 18.6 | 64.2 | 45.8 | 89.6 |
| Acetone | 9.8 | 3.1 | 1.7 | 2.1 |
| MEK | 0.6 | 2.8 | 2.8 | 1.5 |
| EtOAc | 10.9 | — | 6.8 | — |
| AcH | 1.6 | — | — | — |
| EtOH | — | 1.6 | — | 1.2 |
| 2-pentanone | 2.4 | 0.4 | — | 0.3 |
| 2-heptanone | — | — | — | — |
| Others | 11.1 | — | 4.5 | — |
| Water | 26.5 | 20.8 | 24.6 | — |

EXAMPLE II

The same materials and procedure as in Example I were used with the exception that the pyrolysis reactions were performed at 400° C. The results of this series of runs are set forth in Table 2. It will be noted by comparing the results of Tables 1 and 2 that with this catalyst system and the feeds employed, the increase of the pyrolysis temperature from 350° C. to 400° C. gave a sharp increase in the production of methyl ketones, especially acetone and 2-pentanone and a sharp reduction in the amount of monomeric formaldehyde produced.

TABLE 2

Catalyzed Pyrolysis of Acetaldehyde & Ethanol
400° C.

| Run Number | 1 | 2 | 3 | 4 |
|---|---|---|---|---|
| Feed | EtOH | AcH | AcH & EtOH | AcH & H₂O |
| EtOH Conversion, % | 96.0 | — | 74.4 | — |
| AcH Conversion, % | — | 99.6 | 99.8 | 99.0 |
| Product Distribution, wt. percent | | | | |
| CO | 1.8 | 10.3 | 11.9 | 6.4 |
| CO₂ | 23.3 | 43.8 | 26.7 | 42.9 |
| CH₄ | 0.7 | 2.7 | 1.1 | 2.3 |
| C₂-C₄ HC | 9.8 | 2.8 | 4.6 | 2.9 |
| HCHO | 0.8 | 0.7 | 2.3 | 0.1 |
| Acetone | 29.2 | 18.4 | 22.6 | 29.5 |
| MEK | 0.1 | 0.9 | 0.7 | 1.2 |
| EtOAc | 0.4 | — | 0.1 | — |
| AcH | — | — | — | — |
| EtOH | — | — | — | 0.2 |
| 2-pentanone | 16.1 | 7.6 | 10.2 | 14.6 |
| 2-heptanone | 2.3 | — | 1.2 | — |
| Others | 2.8 | — | 5.5 | — |
| Water | 11.5 | 12.8 | 13.1 | — |

EXAMPLE III

Using the same catalyst, apparatus and procedure as in Example I propanol was fed to the reactor and the pyrolysis was performed at 405° C. A 16% conversion of propanol was achieved and the reaction yielded the following product distribution (wt %):

25% 3-pentanone
49% propylpropionate
26% others

EXAMPLE IV

Example III was repeated in the same manner except that the pyrolysis was performed at 450° C. Under these conditions a 94% conversion of propanol was achieved and the production distribution was as follows:

7% 2-butanone
75% 3-pentanone
4% 2-methyl-3-hexanone
2% 4-methyl-3-hexanone
2% 4-methyl-3-heptanone
10% others It is possible to vary certain aspects and other features of the above described invention without departing from the lawful scope or true spirit thereof.

I claim:

1. A process which comprises the step of pyrolyzing an alcohol having 2 to 10 carbon atoms or an aldehyde having 2 to 10 carbon atoms, or both, over a metal oxide catalyst consisting essentially of a major proportion of ferric oxide and a minor proportion of a Group IV-A metal oxide so that at least higher molecular weight ketone or lower molecular weight aldehyde is formed.

2. A process of claim 1 wherein the Group IV-A metal oxide is predominantly a germanium oxide.

3. A process of claim 1 wherein the Group IV-A metal oxide is predominantly germanium dioxide.

4. A process of claim 1 wherein the pyrolysis is conducted in the vapor phase at a temperature of at least about 300° C.

5. A process of claim 1 wherein the feed to the pyrolysis consists essentially of ethanol or acetaldehyde, or both.

6. A process of claim 5 wherein the feed to the pyrolysis consists essentially of a mixture of acetaldehyde and water.

7. A process for the production of a pyrolysis product enriched in formaldehyde which comprises the step of pyrolyzing acetaldehyde over a catalyst consisting essentially of ferric oxide and a minor proportion of a Group IV-A metal oxide at a temperature of about 325° to about 375° C. so that a vaporous product enriched in formaldehyde is formed.

8. A process of claim 7 wherein the feed to the pyrolysis consists essentially of a mixture of acetaldehyde and water.

9. A process of claim 7 wherein the Group IV-A metal oxide is predominantly a germanium oxide.

10. A process of claim 7 wherein the feed to the pyrolysis consists essentially of a mixture of acetaldehyde and water and the catalyst consists essentially of a major proportion of ferric oxide and a minor proportion of germanium dioxide.

11. A process of claim 10 wherein the catalyst contains at least about 90% by weight of ferric oxide and up to about 10% by weight of germanium dioxide.

12. A process for the production of a pyrolysis product enriched in acetone and 2-pentanone which comprises the step of pyrolyzing ethanol or acetaldehyde, or both, over a catalyst consisting essentially of ferric oxide and a minor proportion of a Group IV-A metal oxide at a temperature of about 375° to about 425° C. so that a vaporous product enriched in acetone and 2-pentanone is formed.

13. A process of claim 12 wherein the feed to the pyrolysis consists essentially of a mixture of acetaldehyde and water.

14. A process of claim 12 wherein the Group IV-A metal oxide is predominantly a germanium oxide.

15. A process of claim 12 wherein the catalyst consists essentially of a major proportion of ferric oxide and a minor proportion of germanium dioxide.

16. A process of claim 15 wherein the catalyst contains at least about 90% by weight of ferric oxide and up to about 10% by weight of germanium dioxide.

* * * * *

UNITED STATES PATENT AND TRADEMARK OFFICE
CERTIFICATE OF CORRECTION

PATENT NO. : 4,562,296
DATED : DECEMBER 31, 1985
INVENTOR(S) : DUANE C. HARGIS

It is certified that error appears in the above-identified patent and that said Letters Patent is hereby corrected as shown below:

Column 1, line 61, reads "250°" and should read -- 250°C --.

Column 2, line 63, reads "the form" and should read -- that form --.

Column 5, line 12, reads "ws" and should read -- was --.

Column 5, line 32, reads "three" and should read -- these --.

Signed and Sealed this

Twenty-fifth Day of March 1986

[SEAL]

Attest:

DONALD J. QUIGG

Attesting Officer

Commissioner of Patents and Trademarks